(12) United States Patent
Wei et al.

(10) Patent No.: US 11,022,424 B2
(45) Date of Patent: Jun. 1, 2021

(54) OPTICAL COHERENCE TOMOGRAPHY SYSTEM

(71) Applicant: SVISION IMAGING LIMITED, Henan (CN)

(72) Inventors: Xing Wei, Henan (CN); Bingjie Huang, Henan (CN); Jun Chen, Henan (CN); Xianzhao Peng, Henan (CN)

(73) Assignee: SVISION IMAGING LIMITED, Henan (CN)

( * ) Notice: Subject to any disclaimer, the term of this patent is extended or adjusted under 35 U.S.C. 154(b) by 0 days.

(21) Appl. No.: 16/831,842

(22) Filed: Mar. 27, 2020

(65) Prior Publication Data

US 2020/0225021 A1 Jul. 16, 2020

Related U.S. Application Data

(63) Continuation of application No. PCT/CN2018/103869, filed on Sep. 4, 2018.

(30) Foreign Application Priority Data

Sep. 29, 2017 (CN) .......................... 201710904860.1

(51) Int. Cl.
*G01B 9/02* (2006.01)
*A61B 3/10* (2006.01)

(52) U.S. Cl.
CPC ..... *G01B 9/02091* (2013.01); *G01B 9/02004* (2013.01); *G01B 9/02027* (2013.01); *G01B 9/02059* (2013.01); *A61B 3/102* (2013.01)

(58) Field of Classification Search
CPC ............ G01B 9/02091; G01B 9/02004; G01B 9/02027; G01B 9/02056; G01B 9/02059
See application file for complete search history.

(56) References Cited

U.S. PATENT DOCUMENTS

| 8,947,672 B2 * | 2/2015 | Schmoll | G01B 9/02004 356/497 |
| 2012/0188555 A1 * | 7/2012 | Izatt | G01B 9/02078 356/479 |
| 2017/0231493 A1 * | 8/2017 | Ohmori | A61B 3/1225 351/208 |

FOREIGN PATENT DOCUMENTS

CN 107495921 12/2017

* cited by examiner

*Primary Examiner* — Tarifur R Chowdhury
*Assistant Examiner* — Jonathon Cook
(74) *Attorney, Agent, or Firm* — JCIP Global Inc.

(57) ABSTRACT

An optical coherence tomography system, includes a swept-source laser, a Mach-Zehnder interferometer and a balanced detector. The interferometer includes a first fiber coupler, a second fiber coupler, a sample arm and a reference arm. The reference arm includes a reference arm front section, a reference arm rear section and a delay line. A tail end of the reference arm front section is connected to the reference arm rear section through the delay line. The first fiber coupler is configured to split the output light of the swept-source into a sample light and a reference light and distribute the returned sample light to the second fiber coupler. A difference between the optical path length of a parasitic reflected signal of the delay line reaching the second fiber coupler and the optical path length of the sample light is greater than 8 times the cavity length of the swept-source laser.

9 Claims, 10 Drawing Sheets

OPTICAL COHERENCE TOMOGRAPHY SYSTEM

CROSS-REFERENCE TO RELATED APPLICATION

This application is a continuation of international PCT application serial no. PCT/CN2018/103869, filed on Sep. 4, 2018, which claims the priority benefit of Chinese application no. 201710904860.1, filed on Sep. 29, 2017. The entirety of each of the above-mentioned patent applications is hereby incorporated by reference herein and made a part of this specification.

TECHNICAL FIELD

The invention relates to 3-dimensional imaging technologies, and more particularly relates to a swept-source optical coherence tomography (OCT) system.

BACKGROUND INFORMATION AND PRIOR ART

Optical coherence tomography (OCT) is a 3-dimensional imaging technology that has wide range of applications, especially for biomedical imaging. The OCT technology has many advantages such as high resolution, high imaging speed, and high sensitivity. Since commercial OCT imaging systems first came to market in 1996, the OCT technology has greatly promoted the development of ophthalmic diagnostics. Continuous improvement has also been made in the last two decades towards ever-increasing speed, sensitivity, resolution, and imaging depth.

At present, the most advanced OCT technology is swept-source OCT or SS-OCT, which is based on a laser light source with fast-sweeping wavelengths. A commercial ophthalmic SS-OCT apparatus (PLEX Elite 9000 from Carl Zeiss Meditec, Inc.) was approved by the U. S. Food and Drug Administration (FDA) in 2016. However, due to its high price and complexity, SS-OCT has not yet been widely adopted by ophthalmologists. Today, most commercial ophthalmic OCT systems are based on spectrometers, and the technology is referred to as spectral-domain OCT or SD-OCT.

FIG. 1 is a schematic diagram of an SD-OCT system, and FIG. 2 is a schematic diagram of an SS-OCT system. Both SD-OCT and SS-OCT are based on an optical interference system, which includes a sample arm (abbreviated as SMP in the figure) and a reference arm (abbreviated as REF in the figure), and detects the interference in the frequency domain. Typically, the reference arm includes an adjustable optical delay line for adjusting the optical path length of the reference arm to match the optical path length of the sample arm.

The main difference between SD-OCT and SS-OCT is that SD-OCT uses a low coherence source (abbreviated as LCS in FIG. 1) and a spectrometer (typically consisting of a diffractive grating and a 1-dimensional line-scan camera) to acquire interference spectral signals, whereas SS-OCT uses a swept-source laser and a high-speed photodetector to acquire the interference spectral signals. Both use digital signal processing units (DSPs) to process the spectral signals and reconstruct the OCT image.

For illustration purpose, FIG. 1 and FIG. 2 show only a Michelson interferometer system. Mach-Zehnder interferometer could also be used, as shown in FIG. 3. In FIG. 3, Coupler 1 is a first coupler, Coupler 2 is a second coupler, A' direction is the returned light of the Sample Arm, B' direction is the returned light of the Reference Arm, and the light waves from the sample arm and the reference arm are re-combined at Coupler 2 and the interference signal is detected by the Balanced Detector. For simplicity, a scanning optical device that directs the sample arm light beam to the measured sample is omitted in FIG. 3. As an example, the measured sample in FIG. 3 is an eye, but the description here is not limited to applications in ophthalmology.

The imaging depths of SD-OCT and SS-OCT are limited by different physical limitations. The imaging depth of SD-OCT is determined by the resolution of the spectrometer, and is about several millimeters in air. The imaging depth of SS-OCT is determined by the coherence length of the swept-source, the bandwidth of the optical signal detector, and the sampling frequency, and the imaging depth is typically several millimeters, and may be up to hundreds of millimeters.

The SD-OCT technology has slowly reached maturity over the last decade. At present, most of the low coherence sources used in SD-OCT are super-luminescent diodes (SLDs), which are robust and relatively inexpensive. SS-OCT, on the other hand, is likely to win over SD-OCT in the long run because of its higher imaging speed, larger imaging depth, and higher sensitivity.

Based on the output mode, the swept-source lasers can be divided in two types: single longitudinal mode output and multi-longitudinal mode output. In theory, a single longitudinal mode laser with continuously tunable optical frequency is more suitable for SS-OCT. However, in the current market, the technologically mature and commercially available swept sources are mainly multi-longitudinal mode. For a multi-longitudinal mode swept laser, although the output spectral envelope appears to sweep continuously, the laser spectrum contains discrete comb-like spectral lines due to the existence of multiple longitudinal modes. The frequency spacing between two adjacent longitudinal modes is determined by the cavity length of the swept-source laser.

Simultaneous output of multiple longitudinal modes of a swept source may cause a "coherence revival" effect. In the SS-OCT system, when the optical path length of the sample arm matches that of the reference arm, a strong optical interference signal is observed. When an optical path length difference between the sample arm and the reference arm is exactly an integer multiple of the cavity length of the swept-source laser, a relatively strong optical interference signal is also observed.

The coherence revival effect itself is not necessarily harmful. Researchers can use the coherence revival effect to increase the imaging depth of OCT, and this technique is referred to as "coherence revival multiplexing".

However, coherence revival has an adverse side effect. Unlike SD-OCT, the coherence revival effect in SS-OCT leads to artifacts in the OCT image. In the SD-OCT system, optical interference signal can be obtained only when the optical path length difference between the sample arm and the reference arm is within the imaging depth of the system, and light signals with the optical path length difference greater than the imaging depth do not contribute to the interference signal. For SS-OCT, however, light signals with the optical path length difference greater than the imaging depth could still cause relatively strong interference via the coherence revival effect. As a result, SS-OCT is much more vulnerable towards the artifacts caused by reflection or scattering of components in an optical path. This is one of the technological challenges that have hindered the further development of SS-OCT.

There are known methods to mitigate the problem of the coherence revival artifacts in SS-OCT, one of which is to design the optical and system to keep optical components that are prone to reflection or scattering away from locations that produce the coherence revival artifacts. For example, if the laser cavity length of the swept source is 50 mm, then the optical system should be designed to avoid reflection or scattering from components having optical path length difference equal to an integer multiple of the laser cavity length, which is 0, ±50 mm, ±100 mm, ±150 mm, ±200 mm, etc. However, this method has limitations when the cavity length of the swept-source laser is relatively short. Therefore, this method can only be used when the cavity length of the swept-source laser is much greater than the required imaging depth. Based on this consideration, the cavity length of the swept-source laser in the SS-OCT system is typically greater than 35 mm.

In addition, a typical method for suppressing unwanted reflections in an optical fiber system is to use an optical circulator or isolator. However, the optical isolator cannot easily achieve a sufficient spectral bandwidth, is relatively expensive, and could cause additional light losses and polarization mode dispersion (PMD), thereby reducing the system sensitivity.

Methods to avoid the coherence revival artifacts also include the use of a Fourier-domain mode locking (FDML) laser source or another single longitudinal mode swept laser source (for example, a vertical-cavity surface emitting laser (VCSEL)). The FDML laser source has a very long laser cavity length, and can effectively avoid the coherence revival artifacts. However, these laser sources have not yet reached technological maturity for commercial SS-OCT systems.

In practical optical system design, due to some specific constraints, the above-mentioned mitigation methods may not be applicable. For example, for the coherence revival artifacts caused by stray light of the optical delay line in the reference arm (see below for details), the above-mentioned methods are not effective.

FIG. 4 is an SS-OCT system based on a Mach-Zehnder interferometer. The returned light A' of the sample arm and the returned light B' of the reference arm interfere at a coupler H, and the interference signal is detected by the Balanced Detector. Although interference couplers commonly used in the SS-OCT system are based on optical fibers, most delay lines in the reference arm use a free space optical system. The delay line usually includes fiber tips (E and G in FIG. 4), a collimator, and a reflecting prism (F in FIG. 4). These optical components are likely to cause parasitic reflections. These reflected signals will be coupled back to the optical fiber system of the interferometer through the fiber tip E even if they are very weak. For example, a dashed line in the figure represents the reflected signal C' interfering with the returned light B' of the reference arm at the coupler H through the path E→B→H as shown in FIG. 4. Thereby, the coherence revival artifacts produced by the parasitic reflections of delay line components are superimposed on the OCT image of the measured sample (D in FIG. 4), which may be difficult to differentiate from the true OCT image, as shown in FIG. 5. Because there are many components in the delay line that can produce parasitic reflections and the optical path length of the delay line itself can be adjusted within a certain range, this makes it difficult for the optical system design to ensure that the differences between the optical path lengths of all these components (not only limited to E and G in FIG. 4) and the optical path length of the measured sample (D in FIG. 4) can completely avoid the integer multiples of the cavity length of the swept-source laser (A in FIG. 4).

As mentioned earlier, most OCT systems are based on Michelson or Mach-Zehnder interferometers. For the SS-OCT system based on the Michelson interferometer in FIG. 1 and FIG. 2, the optical path length of the sample arm and the optical path length of the reference arm must be matched to obtain the intended optical interference signal. Similarly, as shown in FIG. 4, for the SS-OCT system based on the Mach-Zehnder interferometer, the optical path length of the delay line needs to be adjusted so that the optical path lengths (OPLs) of the sample arm and the reference arm are matched. Common system design schemes are as follows:

forward optical path length: OPL(B→C→D)≈OPL(B→E→F), and backward optical path length: OPL(D→C→B→H)≈OPL(F→G→H).

Based on such a system design, the coherence revival artifacts due to the parasitic reflections of the delay line components are likely to be present, which affects the structure image of the true sample. For example, the optical path length of the parasitic reflection (path F→E→B→H in FIG. 4) at the reflecting prism F is equal to the optical path length of the measured sample D, thereby producing the coherence revival artifacts that affect the structure image of the true sample or the eye D:

OPL(F→E→B)≈OPL(D→C→B).

Other components in the delay line, such as the fiber tips E and G, are also prone to produce the coherence revival artifacts.

SUMMARY OF THE INVENTION

Object of the invention: in order to solve problems existing in the prior art and suppress coherence revival artifacts caused by stray light of a reference arm in an SS-OCT system, the invention provides a design different from a common OCT system.

Technical solution: an optical coherence tomography (OCT) system includes a swept-source laser, a Mach-Zehnder interferometer and a balanced detector, wherein the interferometer includes a first fiber coupler, a second fiber coupler, a sample arm and a reference arm; the reference arm includes a reference arm front section, a reference arm rear section and a delay line (in one implementation, the delay line itself further includes a third fiber coupler); each fiber coupler includes a first port, a second port, a third port and a fourth port; the output of the swept-source laser is connected to the first port of the first fiber coupler, the second port of the first fiber coupler is connected to the sample arm, the third port of the first fiber coupler is connected to the reference arm front section, and the fourth port of the first fiber coupler is connected to the first port of the second fiber coupler; the tail end of the reference arm front section is connected to the reference arm rear section through the delay line (in one implementation, connection is achieved by the third fiber coupler); the first fiber coupler is configured to split the output light of the swept source into sample light and reference light and distribute the returned sample light to the second fiber coupler; the tail end of the reference arm rear section is connected to the second port of the second fiber coupler; the third port and the fourth port of the second fiber coupler are connected to the balanced detector; the resonant cavity length of the swept-source laser is greater than 35 mm; and a difference between the optical path length of a parasitic reflected signal of the delay line reaching the second fiber coupler and the optical path length of the sample light is greater than 8 times the cavity length of the swept-source laser.

Preferably, the delay line includes fiber tips, collimators, and a reflective optical component; the fiber tips include a fiber tip of the reference arm front section and a fiber tip of the reference arm rear section; the collimators include a transmitting collimator and a receiving collimator; the reference light enters the transmitting collimator through the reference arm front section and is reflected by the reflective optical component; the returned reference light passes to the reference arm rear section through the receiving collimator and reaches the second fiber coupler; and the optical path length of the reference arm front section is greater than the optical path length of the sample arm, with a difference between the two greater than 8 times the cavity length of the swept-source laser.

Preferably, the delay line includes fiber tips, collimators and a reflective optical component; the fiber tips include a fiber tip of the reference arm front section and a fiber tip of the reference arm rear section; the collimators include a transmitting collimator and a receiving collimator; the reference light enters the transmitting collimator through the reference arm front section and is reflected by the reflective optical component; the returned reference light passes to the reference arm rear section through the receiving collimator and reaches the second fiber coupler; the sum of the optical path length of the reference arm front section and the round-trip optical path length of the delay line is L; and L is less than the optical path length of the sample arm, with a difference between L and the optical path length of the sample arm greater than 8 times a cavity length of the swept source.

Preferably, in the delay line, a single-collimator and a third fiber coupler are shared by the reference arm front section and the reference arm rear section; the reference arm front section is connected to the first port of the third fiber coupler; the second port of the third fiber coupler is connected to the single-collimator; the reference light enters the single-collimator, reaches a reflective optical component, is reflected back along the same path, and passes to the third port of the third fiber coupler; the third port of the third fiber coupler is connected to the second port of the second fiber coupler; and the optical path length of the reference arm front section is greater than the optical path length of the sample arm, with a difference between the two greater than 8 times the cavity length of the swept-source laser. In this implementation, the delay line is simplified, and the single-collimator delay line is more stable and easier to assemble. Moreover, the third fiber coupler has an extra fourth port, which can be used for other purposes, such as laser power monitoring.

Preferably, in the delay line, a single-collimator and a third fiber coupler are shared by the reference arm front section and the reference arm rear section; the reference arm front section is connected to the first port of the third fiber coupler; the second port of the third fiber coupler is connected to the single-collimator; the reference light enters the single-collimator, reaches a reflective optical component through, is reflected back along the same path, and passes to the third port of the third fiber coupler; the third port of the third fiber coupler is connected to the second port of the second fiber coupler; the sum of the optical path length of the reference arm front section and the round-trip optical path length of the delay line is L; and L is less than the optical path length of the sample arm, with a difference between L and the optical path length of the sample arm greater than 8 times the cavity length of the swept-source laser.

Preferably, the reflective optical component is a corner reflector.

Advantages: the OCT system based on the invention increases the order of the coherence revival artifacts by increasing or decreasing the optical path length of the parasitic or stray reflected light of the delay line components, thereby achieving the effect of suppressing the coherence revival artifacts. Compared with the prior art, the OCT system can achieve sufficient spectral width, is simple and relatively inexpensive, does not cause additional optical losses or polarization mode dispersion (PMD), and can ensure the sensitivity of the system.

DETAILED DESCRIPTION OF THE INVENTION

Figure 1:
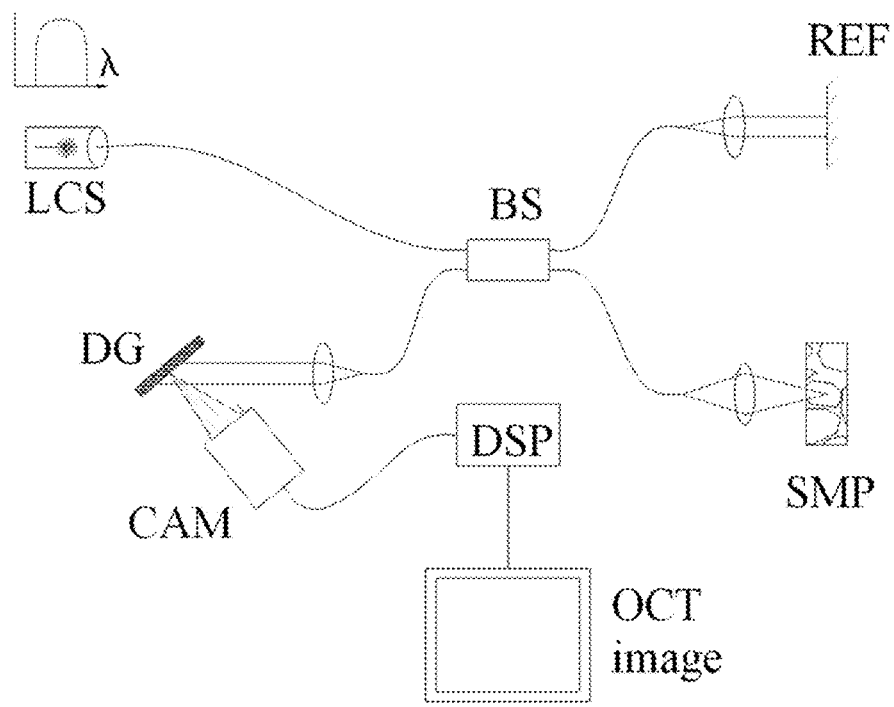
FIG. 1 is a schematic diagram of an SD-OCT system.
Figure 2:
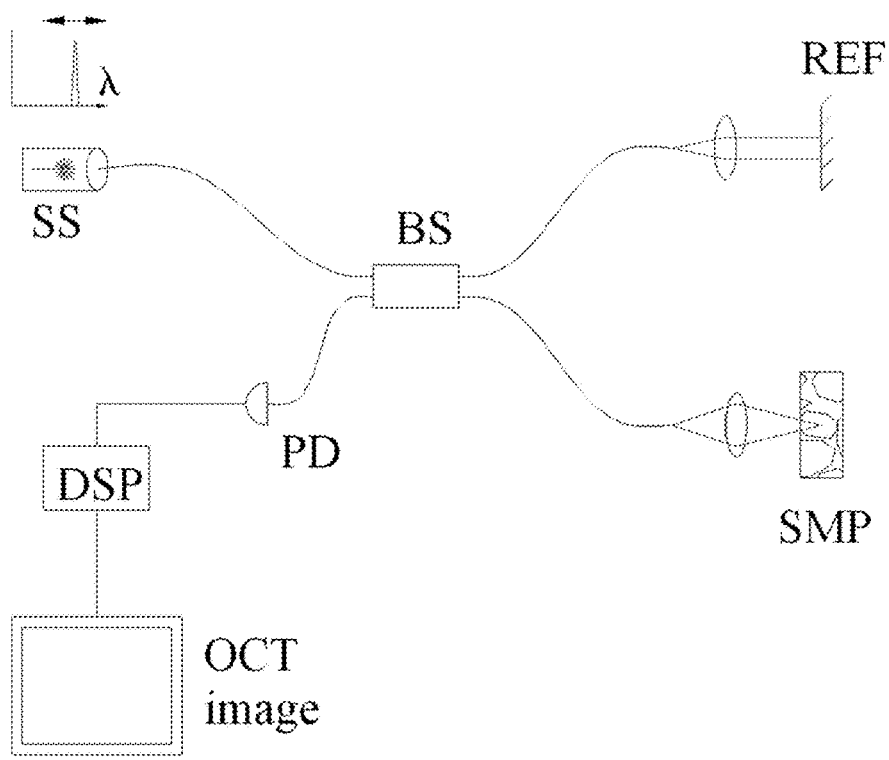
FIG. 2 is a schematic diagram of an SS-OCT system.
Figure 3:
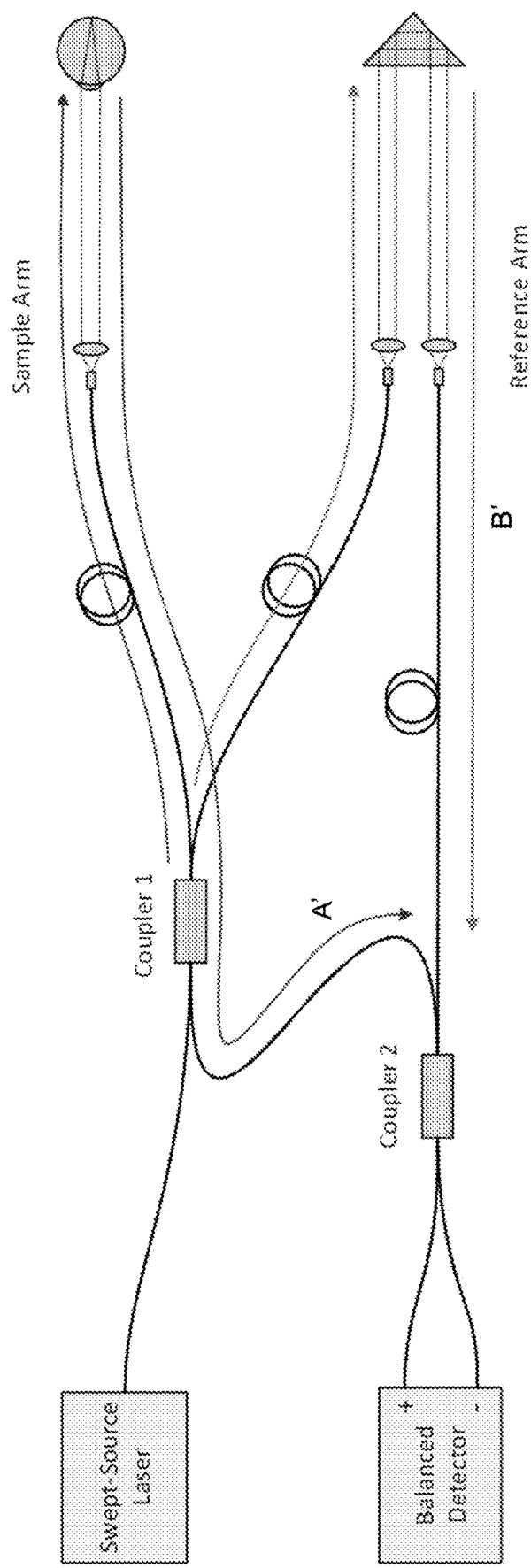
FIG. 3 is a schematic diagram of the SS-OCT system based on a Mach-Zehnder interferometer.
Figure 4:
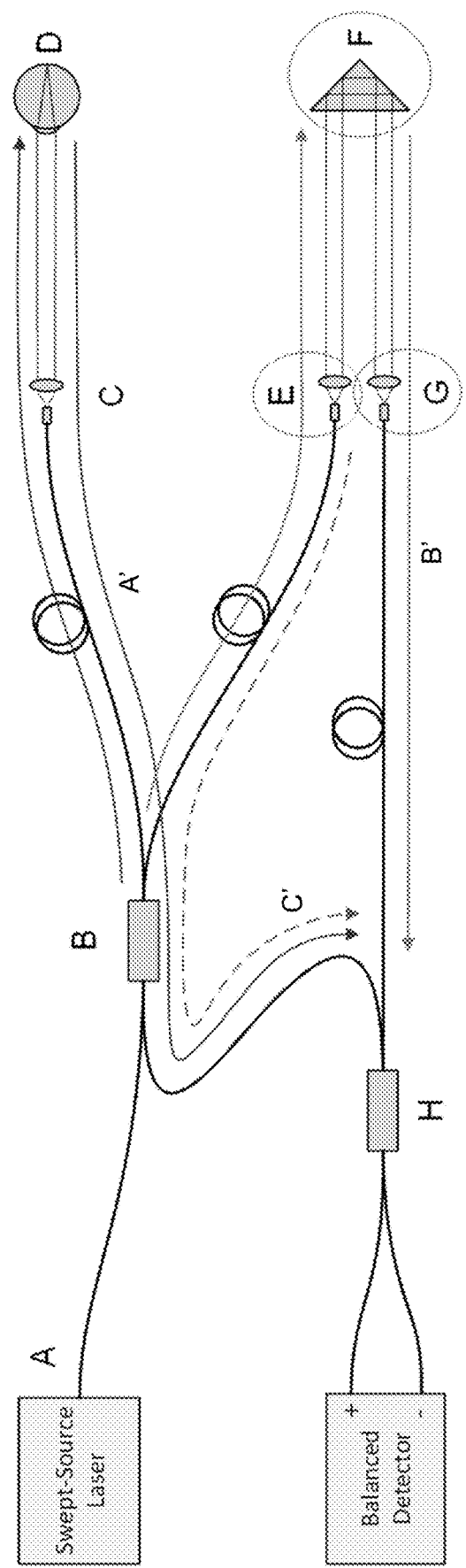
FIG. 4 is a schematic diagram of parasitic reflections of a delay line component.
Figure 5:
FIG. 5 is an example OCT image with coherence revival artifacts caused by the parasitic reflections of delay line components.
Figure 6:
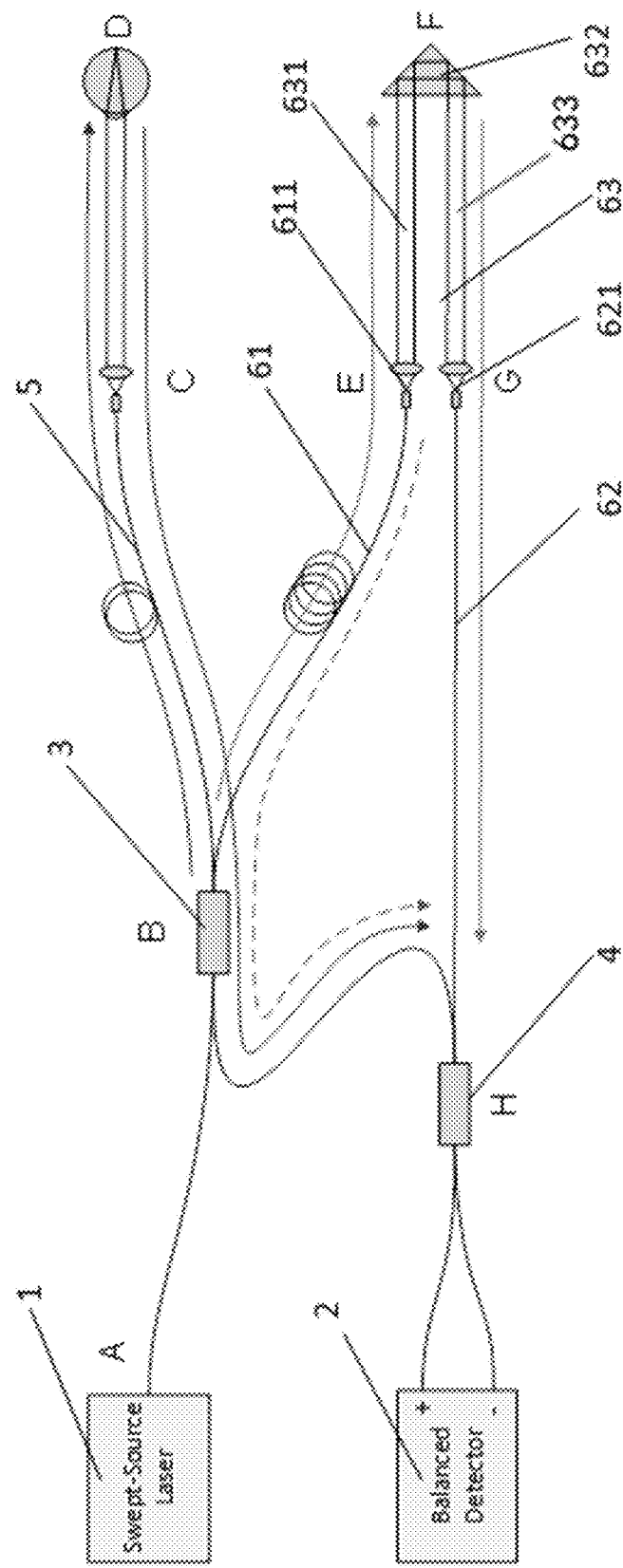
FIG. 6 is a schematic diagram of an SS-OCT system of Embodiment I.

The invention will be further described below with reference to the accompanying drawings and specific embodiments.

Embodiment I

An optical coherence tomography (OCT) system includes a swept-source laser 1, a Mach-Zehnder interferometer, and a balanced detector 2. The interferometer includes a first fiber coupler 3, a second fiber coupler 4, a sample arm 5 and a reference arm. The reference arm includes a reference arm front section 61, a reference arm rear section 62 and a delay line 63. Each of the first fiber coupler 3 and the second fiber coupler 4 includes a first port, a second port, a third port and a fourth port; the output of the swept-source laser 1 is connected to the first port of the first fiber coupler 3. The second port of the first fiber coupler 3 is connected to the sample arm 5. The third port of the first fiber coupler 3 is connected to the reference arm front section 61. The fourth port of the first fiber coupler 3 is connected to the first port of the second fiber coupler 4. The tail end of the reference arm front section 61 is connected to the reference arm rear section 62 through the delay line 63. The first fiber coupler 3 is configured to split output light of the swept-source laser 1 into sample light and reference light and distribute the returned sample light to the second fiber coupler 4. The tail end of the reference arm rear section 62 is connected to the second port of the second fiber coupler 4. The third port and the fourth port of the second fiber coupler 4 are connected to the balanced detector 2. The laser cavity length of the swept-source laser is greater than 35 mm.

The delay line 63 includes fiber tips, collimators and a reflective optical component 632 (a corner reflector in the present embodiment). The fiber tips include a fiber tip 611 of the reference arm front section and a fiber tip 621 of the reference arm rear section. The collimators include a transmitting collimator 631 and a receiving collimator 633. The reference light enters the incident collimator 631 through the reference arm front section 61 and is reflected by the reflective optical component 632, and the returned reference light passes to the reference arm rear section 62 through the reflective collimator 633 and reaches the second fiber coupler 4.

Figure 7:
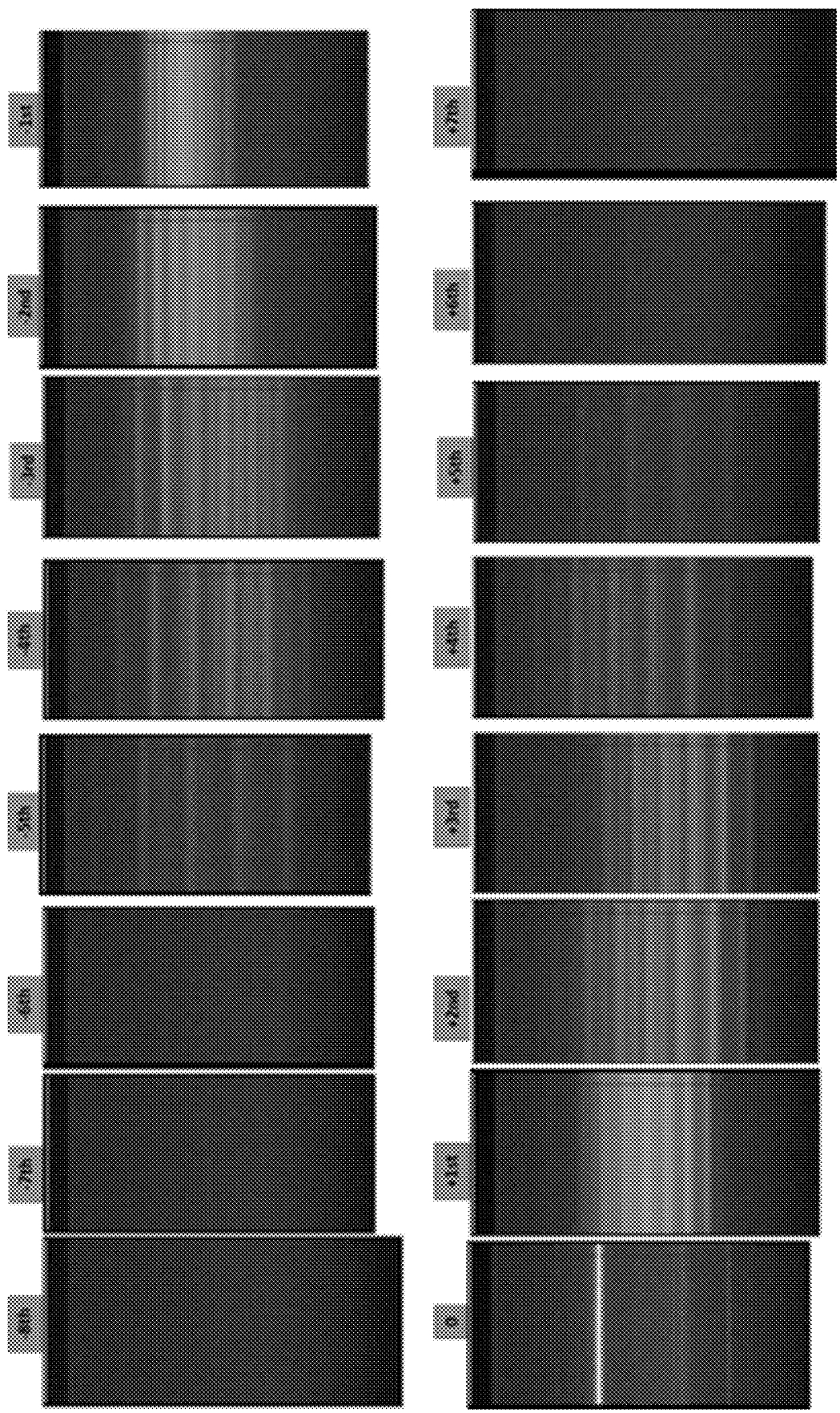
FIG. 7 shows images of coherence revival artifacts of different orders.
Figure 8:
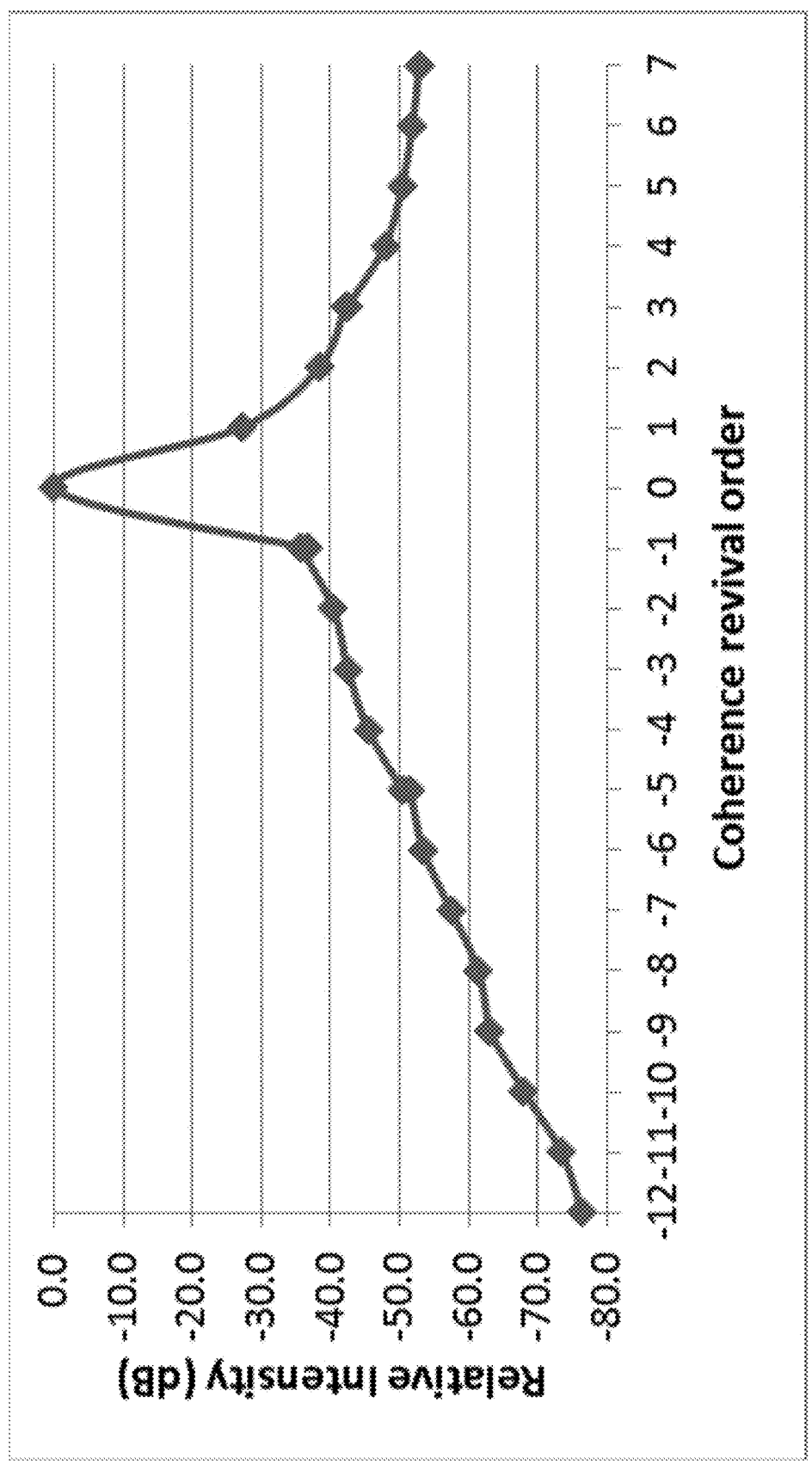
FIG. 8 shows the relative artifact signal intensity as a function of the order of coherence revival.
Figure 9:
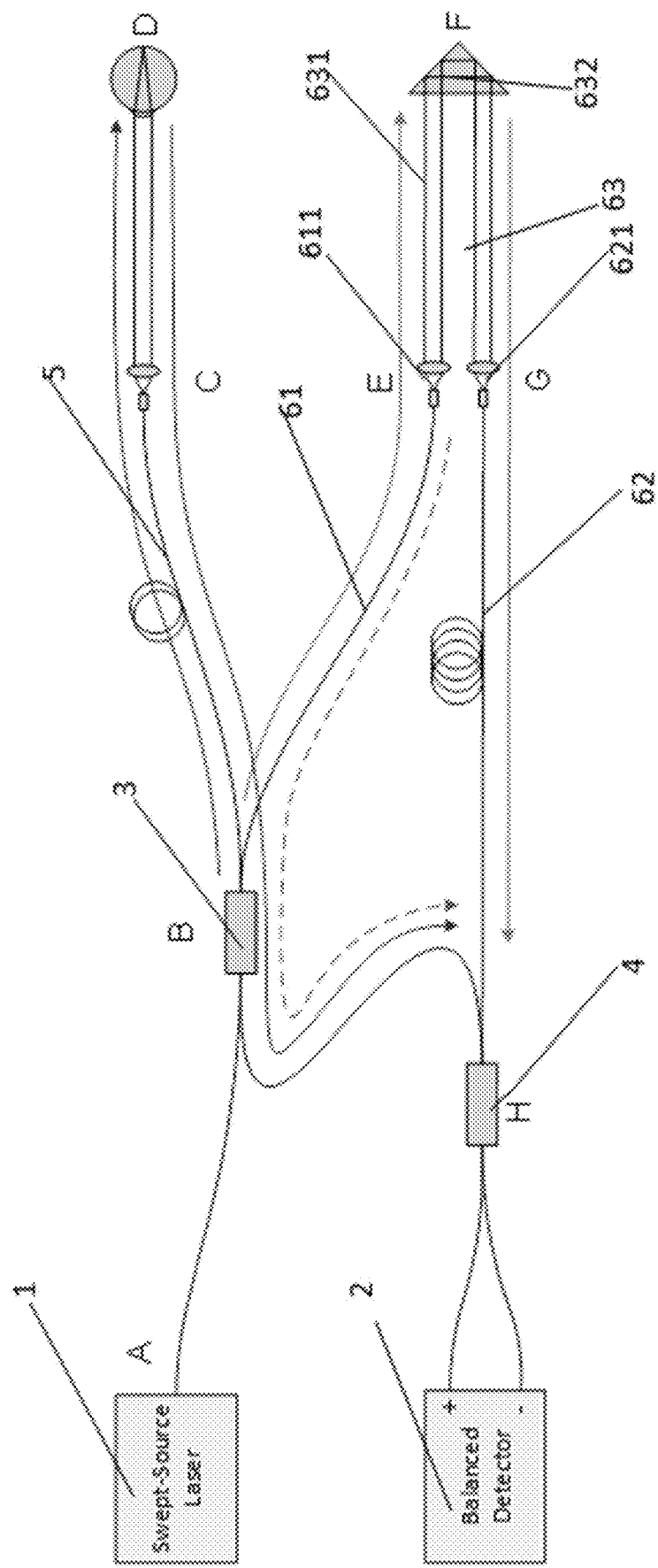
FIG. 9 is a schematic diagram of an SS-OCT system of Embodiment II.

In the present embodiment, by decreasing a fiber length of the reference arm rear section 62 and increasing the fiber length of the reference arm front section 61, a total optical path length of B→E→F→G→H remains unchanged. In this way, an optical path length OPL(B→E) of the reference arm front section will be much greater than the optical path length OPL(B→C→D) of the sample arm, with an optical path length difference L' between them. L' should be greater than N times the cavity length of the swept-source laser, and N is a positive integer. Experiments show that when N is greater than 8, the effect of coherence revival artifacts on the OCT image is negligible. Experimental results of a specific swept source are shown in FIG. 7 and FIG. 8. A "+" sign for the order in FIG. 7 indicates that the optical path length of the sample arm is greater than the optical path length of the reference arm, and a "−" sign for the order indicates that the optical path length of the sample arm is less than the optical path length of the reference arm. In the present embodiment, if the cavity length of the swept-source laser is 50 mm, the optical path length difference between the reference arm front section and the sample arm should be greater than 400 mm, and if the cavity length of the swept-source laser is 40 mm, the optical path length difference should be greater than 320 mm. That is, the following condition needs to be met:

OPL(B→E)>OPL(B→C→D)+8×cavity length of swept-source laser.

Embodiment II

Embodiment II is different from Embodiment I in that Embodiment II achieves the same effect of suppressing the coherence revival artifacts by increasing the fiber length of the reference arm rear section 62 and decreasing the fiber length of the reference arm front section 61. Other parts of the system are the same as those in Embodiment I.

Let us assume that the sum of the optical path length of the reference arm front section 61 and the round-trip optical path length of the delay line 63 be L, then L should be less than the optical path length of the sample arm, with a difference greater than 8 times the cavity length of the swept-source laser. That is, the following condition needs to be met:

OPL(B→E→F→G)<OPL(B→C→D)−8×cavity length of swept-source laser.

Embodiment III

The delay line 63 in Embodiment III is different from that in Embodiment I and Embodiment II. In the delay line 63, a single-collimator 631 (which serves as both the transmitting collimator and the receiving collimator) and a third fiber coupler 7 are shared by the reference arm front section and the reference arm rear section. The third fiber coupler 7 includes a first port, a second port and a third port. The reference arm front section 61 is connected to the first port of the third fiber coupler 7. The second port of the third fiber coupler 7 is connected to the single-collimator. The reference light enters the single-collimator, reaches the reflective optical component 632 (a corner reflector in the present embodiment), is reflected back along the same path, and passes to the third port of the third fiber coupler 7. The third port of the third fiber coupler 7 is connected to the second port of the second fiber coupler 4. Other parts are the same as those in Embodiment I and Embodiment II.

Figure 10:
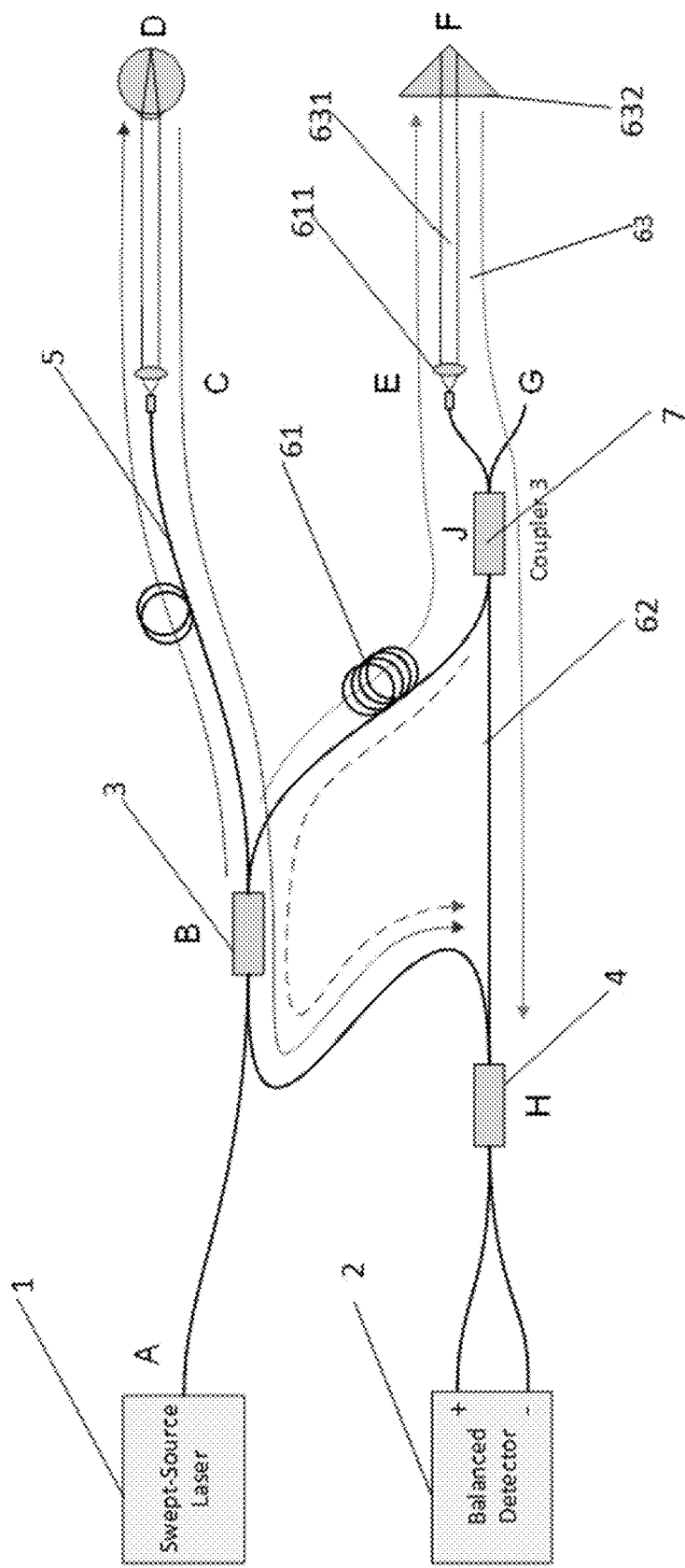
FIG. 10 is a schematic diagram of an SS-OCT system of Embodiment III.

As shown in FIG. 10, the optical path length of the sample arm matches the optical path length of the reference arm, which meets the following condition:

OPL(B→C→D→C→B→H)≈OPL(B→J→E→F→E→J→H).

Parasitic reflected light from components in the delay line is coupled back to the interference system through the fiber tip 611 of the reference arm front section, and passes to the second fiber coupler 4 through the third fiber coupler 7 and the first fiber coupler 3 to interfere with the returned light of the reference arm. It should be particularly noted that, due to the existence of the third fiber coupler 7, coupling efficiency of the parasitic reflected light increases, and the coherence revival artifacts are more severe. The optical path length of the reference arm front section 61 should be greater than the optical path length of the sample arm 5, and the difference between them should be greater than 8 times the cavity length of the swept-source laser. That is, the following condition needs to be met to achieve the purpose of suppressing the coherence revival artifacts:

OPL(B→J→E)>OPL(B→C→D)+8×cavity length of swept-source laser.

Alternatively, let us assume that the sum of the optical path length of the reference arm front section 61 and the round-trip optical path length of the delay line 63 be L, then L should be less than the optical path length of the sample arm 5, with a difference greater than 8 times the cavity length of the swept-source laser, that is:

OPL(B→J→E→F→E)<OPL(B→C→D)−8×cavity length of swept-source laser.

Compared with Embodiment I and Embodiment II, in Embodiment III of the invention as shown in FIG. 10, the delay line 63 is simplified, since the single-collimator is more stable and easier to assemble. Moreover, the third fiber coupler 7 has an extra fourth port G, which can be used for other purposes, such as laser power monitoring.

Figure 11:
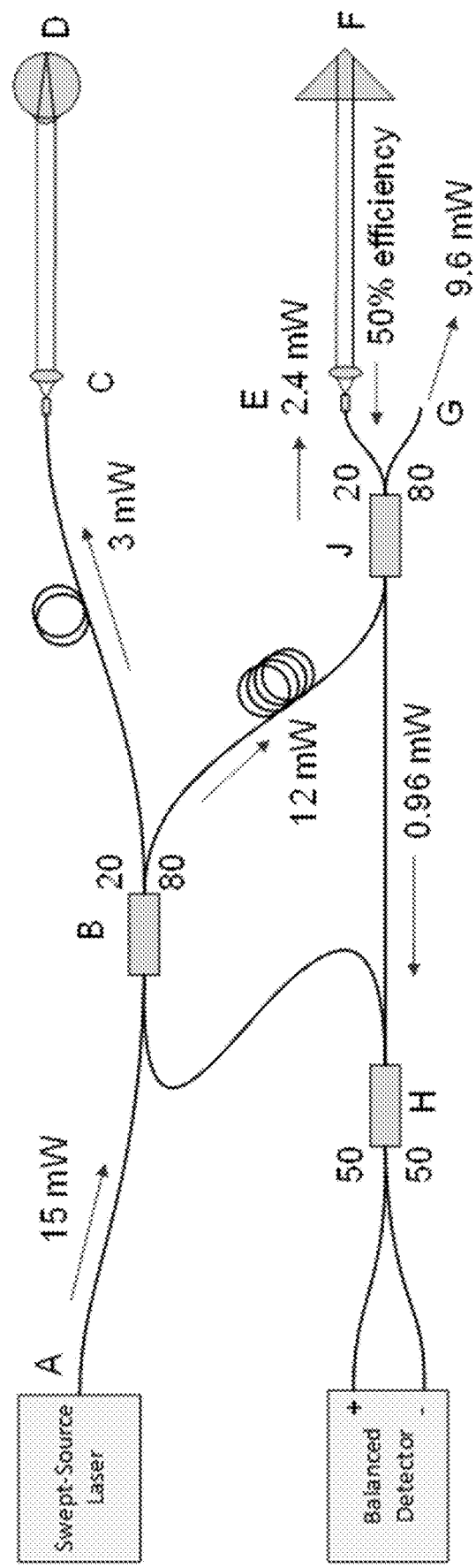
FIG. 11 is a schematic diagram showing typical coupler splitting ratios and optical power values of Embodiment III.

FIG. 11 shows typical coupler splitting ratios and optical power values of Embodiment III. For the purpose of illustration, the power calculation is simplified here, coupling losses in the system are ignored, and the reflection efficiency of the delay line is assumed to be 50%.

In addition to the optical power values shown at different locations in FIG. 11, the power of the light reflected by the delay line back to the interferometer system (path J→B→H in FIG. 10) is 2.4×0.5×0.2×0.2=0.048 mW, which is approximately 5% of the reference arm optical power (0.96 mW). Although the light will only increase the background noise level by 0.2 dB, it has a much stronger intensity than the light signal reflected back from the sample arm. If the optical system design does not meet the optical path difference condition described above (coherence revival order N>8), strong coherence revival artifacts would arise.

By selecting the following fiber lengths (FIG. 11), the order of the coherence revival artifacts can be easily increased beyond 20, which is much greater than the requirement of being higher than the 8th order mentioned above (the higher the order, the better the effect of suppressing the coherence revival artifacts). It is assumed here that the cavity length of the swept-source laser is 50 mm, and the optical path lengths of the optical couplers are ignored. In the calculation of OPL, the group refractive index of the optical fiber is about 1.47.

| Fiber or Air | BJ | JE | EF | BC | CD | BH | HJ |
|---|---|---|---|---|---|---|---|
| Length (mm) | 2000 | 1000 | 150 | 1830 | 400 | 200 | 200 |

Forward sample arm optical path length OPL(B→C→D)=1830×1.47+400≈3090 mm.

Backward sample arm optical path length OPL(D→C→B→H)=400+(1830+200)×1.47≈3384 mm.

Total sample arm optical path length OPL(B→C→D→C→B→H)≈3090+3384=6474 mm.

Total reference arm optical path length OPL(B→J→E→F→E→J→H)=(2000+1000×2+200)×1.47+150×2=6474 mm.

Shortest forward optical path length of stray light OPL(B→J→E)≈(2000+1000)×1.47≈4410 mm.

OPL(B→J→E)−OPL(B→C→D)≈4410−3090=1320 mm≈26×cavity length of swept-source laser.

The optical power reflected back to the swept source is 2.4×0.5×0.2×0.8=0.192 mW (not shown in FIG. 11), which is about 1.3% of the output power of the light source. The swept-source laser must tolerate at least 1.3% of optical back reflection.

Although the above three embodiments have different designs, the purpose is the same: to create a difference between the optical path length of the parasitic or stray reflected light from the delay line and the optical path length of the sample light, the difference being greater than 8 times the cavity length of the swept-source laser, by increasing or decreasing the optical path length of the parasitic or stray reflected light, thereby achieving the purpose of suppressing the coherence revival artifacts.

What is claimed is:

1. An optical coherence tomography (OCT) system, comprising:
   a swept-source laser;
   a Mach-Zehnder interferometer; and
   a balanced detector,
   wherein the Mach-Zehnder interferometer comprises a first fiber coupler, a second fiber coupler, a sample arm and a reference arm; the reference arm comprises a reference arm front section, a reference arm rear section and a delay line; each of the first fiber coupler and the second fiber coupler comprises a first port, a second port, a third port and a fourth port; an output of the swept-source laser is connected to the first port of the first fiber coupler, the second port of the first fiber coupler is connected to the sample arm, the third port of the first fiber coupler is connected to the reference arm front section, and the fourth port of the first fiber coupler is connected to the first port of the second fiber coupler; a tail end of the reference arm front section is connected to the reference arm rear section through the delay line; the first fiber coupler is configured to split an output light of the swept-source laser into a sample light and a reference light and distribute the returned sample light to the second fiber coupler; a tail end of the reference arm rear section is connected to the second port of the second fiber coupler; the third port and the fourth port of the second fiber coupler are connected to the balanced detector; a resonant cavity length of the swept-source laser is greater than 35 mm; and a difference between an optical path length of a parasitic or a stray reflected signal of the delay line reaching the second fiber coupler and an optical path length of the sample light is greater than 8 times the resonant cavity length of the swept-source laser.

2. The OCT system of claim 1, wherein the delay line comprises fiber tips, collimators and a reflective optical component; the fiber tips comprise a fiber tip of the reference arm front section and a fiber tip of the reference arm rear section; the collimators comprise a transmitting collimator and a receiving collimator; the reference light enters the transmitting collimator through the reference arm front section and is reflected by the reflective optical component; the returned reference light passes to the reference arm rear section through the receiving collimator and reaches the second fiber coupler; and an optical path length of the reference arm front section is greater than an optical path length of the sample arm, with a difference between the two greater than 8 times the cavity length of the swept-source laser.

3. The OCT system of claim 1, wherein the delay line comprises fiber tips, collimators and a reflective optical component; the fiber tips comprise a fiber tip of the reference arm front section and a fiber tip of the reference arm rear section; the collimators comprise a transmitting collimator and a receiving collimator; the reference light enters the transmitting collimator through the reference arm front section and is reflected by the reflective optical component; the returned reference light passes to the reference arm rear section through the receiving collimator and reaches the second fiber coupler; a sum of an optical path length of the reference arm front section and a round-trip optical path length of the delay line is L; and L is less than an optical path length of the sample arm, with a difference between the two greater than 8 times the cavity length of the swept-source laser.

4. The OCT system of claim 1, wherein the delay line comprises a single-collimator a third fiber coupler, which are shared by the reference arm front section and the reference arm rear section; the third fiber coupler comprises a first port, a second port and a third port; the reference arm front section is connected to the first port of the third fiber coupler; the second port of the third fiber coupler is connected to the single-collimator; the reference light enters the single-collimator, reaches a reflective optical component, is reflected back along the same path, and passes to the third port of the third fiber coupler; the third port of the third fiber coupler is connected to the second port of the second fiber coupler; and an optical path length of the reference arm front section is greater than an optical path length of the sample arm, with a difference between the two greater than 8 times the cavity length of the swept-source laser.

5. The OCT system of claim 1, wherein the delay line comprises a single-collimator and a third fiber coupler, which are shared by the reference arm front section and the reference arm rear section; the third fiber coupler comprises a first port, a second port and a third port; the reference arm front section is connected to the first port of the third fiber coupler; the second port of the third fiber coupler is connected to the single-collimator; the reference light enters the single-collimator, reaches a reflective optical component, is reflected along the same path, and passes to the third port of the third fiber coupler; the third port of the third fiber coupler is connected to the second port of the second fiber coupler; a sum of an optical path length of the reference arm front section and a round-trip optical path length of the delay line is L, and L is less than an optical path length of the sample arm, with a difference between the two greater than 8 times the cavity length of the swept-source laser.

6. The OCT system of claim 2, wherein the reflective optical component is a corner reflector.

7. The OCT system of claim 3, wherein the reflective optical component is a corner reflector.

8. The OCT system of claim 4, wherein the reflective optical component is a corner reflector.

9. The OCT system of claim 5, wherein the reflective optical component is a corner reflector.

* * * * *